United States Patent
Tateshima

(10) Patent No.: US 9,872,735 B2
(45) Date of Patent: Jan. 23, 2018

(54) APPARATUS AND METHODS FOR PRECISE STENT PLACEMENT

(71) Applicant: THE REGENTS OF THE UNIVERSITY OF CALIFORNIA, Oakland, CA (US)

(72) Inventor: Satoshi Tateshima, Pacific Palisades, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 75 days.

(21) Appl. No.: 14/643,215

(22) Filed: Mar. 10, 2015

(65) Prior Publication Data
US 2015/0238278 A1   Aug. 27, 2015

Related U.S. Application Data

(63) Continuation of application No. PCT/US2013/057630, filed on Aug. 30, 2013.
(Continued)

(51) Int. Cl.
*A61B 19/00*   (2006.01)
*A61F 2/95*   (2013.01)
(Continued)

(52) U.S. Cl.
CPC ............. *A61B 19/54* (2013.01); *A61B 90/39* (2016.02); *A61F 2/82* (2013.01); *A61F 2/95* (2013.01);
(Continued)

(58) Field of Classification Search
CPC ....... A61B 19/54; A61B 90/92; A61F 2/2427; A61F 2/243; A61F 2/2433; A61F 2/2436;
(Continued)

(56) References Cited

U.S. PATENT DOCUMENTS

| 6,078,832 A | 6/2000 | Lenker et al. |
| 6,730,119 B1 | 5/2004 | Smalling |

(Continued)

FOREIGN PATENT DOCUMENTS

| EP | 1897584 A1 | 3/2008 |
| WO | 2009-129199 A1 | 10/2009 |

OTHER PUBLICATIONS

Korean Intellectual Property Office (KIPO), International Search Report and Written Opinion, PCT/US2013/057630, dated Dec. 16, 2013, pp. 1-13, with claims searched, pp. 14-19, corresponding to U.S. Appl. No. 14/643,215 herein.
(Continued)

*Primary Examiner* — Eric Rosen
*Assistant Examiner* — Mikail Mannan
(74) *Attorney, Agent, or Firm* — O'Banion & Ritchey LLP; John P. O'Banion

(57) ABSTRACT

A micro-catheter delivery system that includes radio-opaque marker bands optimized for the purpose of length reference to assist the operating physician to estimate the length of a tortuous lesion and to anticipate foreshortening of stents with multiple sizes. The radio-opaque maker bands are positioned at the distal end of a stent delivery catheter at a certain intervals acts like a ruler. In another embodiment, a stent delivery system includes a stent delivery wire with one or more radio-opaque markers distanced from the stent distal end for indicating the non-restrained length of the stent when discharged from the delivery catheter.

22 Claims, 14 Drawing Sheets

Related U.S. Application Data

(60) Provisional application No. 61/700,741, filed on Sep. 13, 2012, provisional application No. 61/700,300, filed on Sep. 12, 2012.

(51) Int. Cl.
*A61F 2/82* (2013.01)
*A61F 2/966* (2013.01)
*A61M 25/01* (2006.01)
*A61M 25/00* (2006.01)
*A61B 90/00* (2016.01)

(52) U.S. Cl.
CPC ...... *A61F 2/966* (2013.01); *A61B 2090/3966* (2016.02); *A61B 2090/3983* (2016.02); *A61F 2002/823* (2013.01); *A61F 2250/0098* (2013.01); *A61M 25/0111* (2013.01); *A61M 2025/0042* (2013.01)

(58) Field of Classification Search
CPC .. A61F 2/95; A61F 2/954; A61F 2/958; A61F 2/962; A61F 2/966; A61F 2002/9505; A61F 2002/9517; A61F 2002/9522; A61F 2002/9528; A61F 2002/9534; A61F 2/02; A61F 2/286; A61F 2/295; A61M 2205/32; A61M 25/0108
USPC ........................................................ 623/1.11
See application file for complete search history.

(56) References Cited

U.S. PATENT DOCUMENTS

| | | | |
|---|---|---|---|
| 6,989,024 B2 | 1/2006 | Hebert et al. | |
| 2007/0027522 A1* | 2/2007 | Chang | A61F 2/013 623/1.11 |
| 2010/0016940 A1* | 1/2010 | Shokoohi | A61F 2/856 623/1.11 |
| 2010/0331960 A1* | 12/2010 | Clerc | A61F 2/95 623/1.15 |
| 2011/0106238 A1* | 5/2011 | Williamson | A61F 2/915 623/1.16 |
| 2012/0232528 A1* | 9/2012 | Eli | A61M 25/0108 604/529 |
| 2014/0121744 A1* | 5/2014 | Kusleika | A61F 2/852 623/1.11 |
| 2014/0180387 A1* | 6/2014 | Khenansho | A61F 2/966 623/1.12 |
| 2014/0228943 A1* | 8/2014 | Stigall | A61F 2/2436 623/2.11 |

OTHER PUBLICATIONS

Angiodynamics, "Accu-Vu Sizing Cathether", brochure, 2011 AngioDynamics, Inc., MLC 121 U.S. Rev G 09/11, pp. 1-4.

\* cited by examiner

APPARATUS AND METHODS FOR PRECISE STENT PLACEMENT

CROSS-REFERENCE TO RELATED APPLICATIONS

This application is a 35 U.S.C. §111(a) continuation of PCT international application number PCT/US2013/057630 filed on Aug. 30, 2013, incorporated herein by reference in its entirety, which claims priority to, and the benefit of, U.S. provisional patent application Ser. No. 61/700,741 filed on Sep. 13, 2012, incorporated herein by reference in its entirety, and U.S. provisional patent application Ser. No. 61/700,300 filed on Sep. 12, 2012, incorporated herein by reference in its entirety. Priority is claimed to each of the foregoing applications.

The above-referenced PCT international application was published as PCT International Publication No. WO 2014/042900 on Mar. 20, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to endovascular delivery systems and methods, and more particularly to systems and methods for delivery of expandable stents.

2. Description of Related Art

Current endovascular procedures use a metallic expandable stent to expand a lesion or to cover a target lesion. There is an increase in the use of stents due to advancements in biomaterial technology. For example, intracranial aneurysms had been treated only by endovascular coiling or open-surgical clipping until recently; but now those aneurysms can also be treated by using a stent that reduces the blood flow into the target aneurysm and induces complete thrombosis. In order to successfully treat an aneurysm with a stent, it is crucial to cover the aneurysm lesion completely with the stent. Any uncovered area in the aneurysm neck may make the stent procedure ineffective. Therefore, if an uncovered area occurs, an additional stent may need to be placed to completely cover across the aneurysm lesion. This applies not only to aneurysms, but also to stenotic/narrowing lesions. An atherosclerotic plaque covered by a stent should bridge the proximal to the distal normal arterial segment. Thus, the capacity to accurately place a stent across the lesion is a critically important element in endovascular stenting procedure.

There are generally two different types of stents: a laser-cut stent and a braided stent. There are pros and cons for each type of the stent. The most significant limitation of a braided stent is a phenomenon called "foreshortening," which is defined as the change in the length of the stent from a constrained (i.e. compressed) state to an unconstrained (i.e. expanded) state. Although the degree of foreshortening is most significant in a braided stent, it may occur in a micro-machined or laser-cut stent as well. The degree of foreshortening with certain kinds of braided stents can be as large as 100%. This foreshortening poses a challenge to the treating physicians to place a stent very accurately.

Referring to FIG. 1, a stent is generally delivered to a target lesion via a catheter and delivery wire 12. When a braided stent is squeezed in a delivery catheter, the stent becomes longer (elongated stent 10b). Once the stent is being pushed out of the delivery catheter, the stent expands in the target vessel and it becomes shorter (foreshortened stent 10a). This foreshortening phenomenon must be taken into account when a braided stent needs to be placed in a lesion with high accuracy. A physician must therefore anticipate the degree of foreshortening during the stent placement, which requires a certain amount of training and clinical experiences. Nevertheless, it is virtually impossible to achieve 100% accuracy as long as the procedure depends on "anticipation" or "experience."

Another challenge for the accurate stent placement is tortuous anatomy. It is difficult to control the position of delivery catheter and also to anticipate the shape and position of a stent in a curvy target lesion. Endovascular stenting procedures are performed under a 2-dimensional fluoroscopic X-ray imaging guidance. Even with the use of multiple angle fluoroscopic images (for example, bi-plane digital subtraction angiography machine), there is an intrinsic challenge in making a real time estimate on the length of a lesion in a tortuous 3-dimensional anatomy projected onto a 2-dimensional fluoroscopic view.

BRIEF SUMMARY OF THE INVENTION

One aspect of the invention is a micro-catheter delivery system that includes radio-opaque marker bands optimized for the purpose of length reference (i.e. position indicator) to assist the operating physician to estimate the length of a tortuous lesion and to anticipate foreshortening of stents with multiple sizes. In order to accommodate to various anatomies and various stent sizes, the radio-opaque maker bands positioned at the distal end of a stent delivery catheter at certain intervals acts like a ruler, which can be used as a reference of length of the lesion, even in a 2-dimensional projection image.

In another aspect, a stent delivery system is provided that includes a stent delivery wire with one or more radio-opaque markers distanced from the stent distal end for indicating the non-restrained length of the stent when discharged from the delivery catheter.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
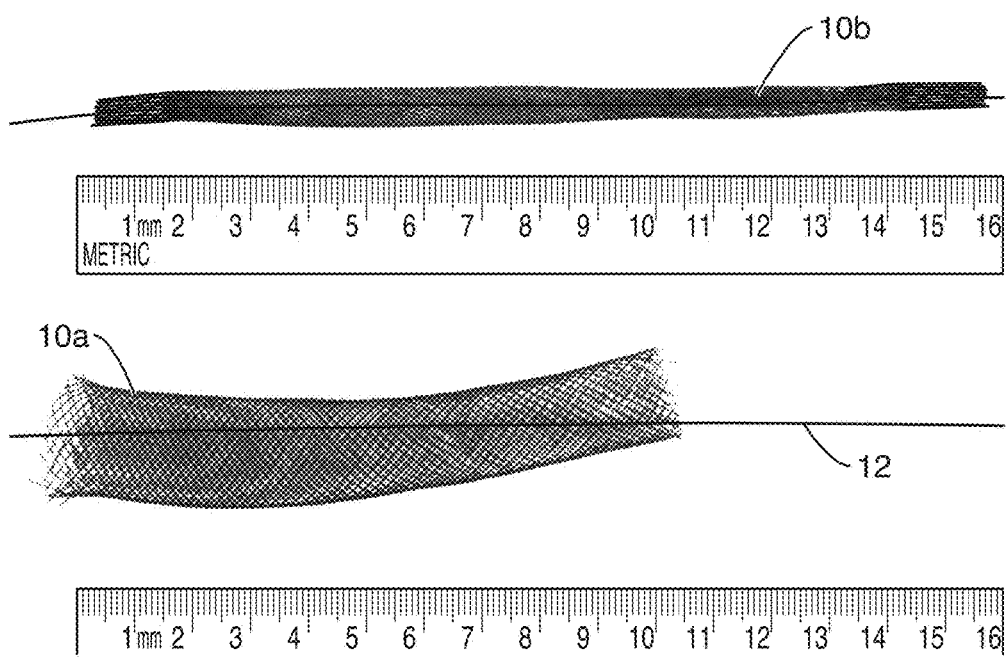
FIG. 1 is an image of an exemplary prior art stent and delivery wire, with the stent shown in an expanded, elongate configuration, and another stent in a non-constrained configuration.
Figure 2:
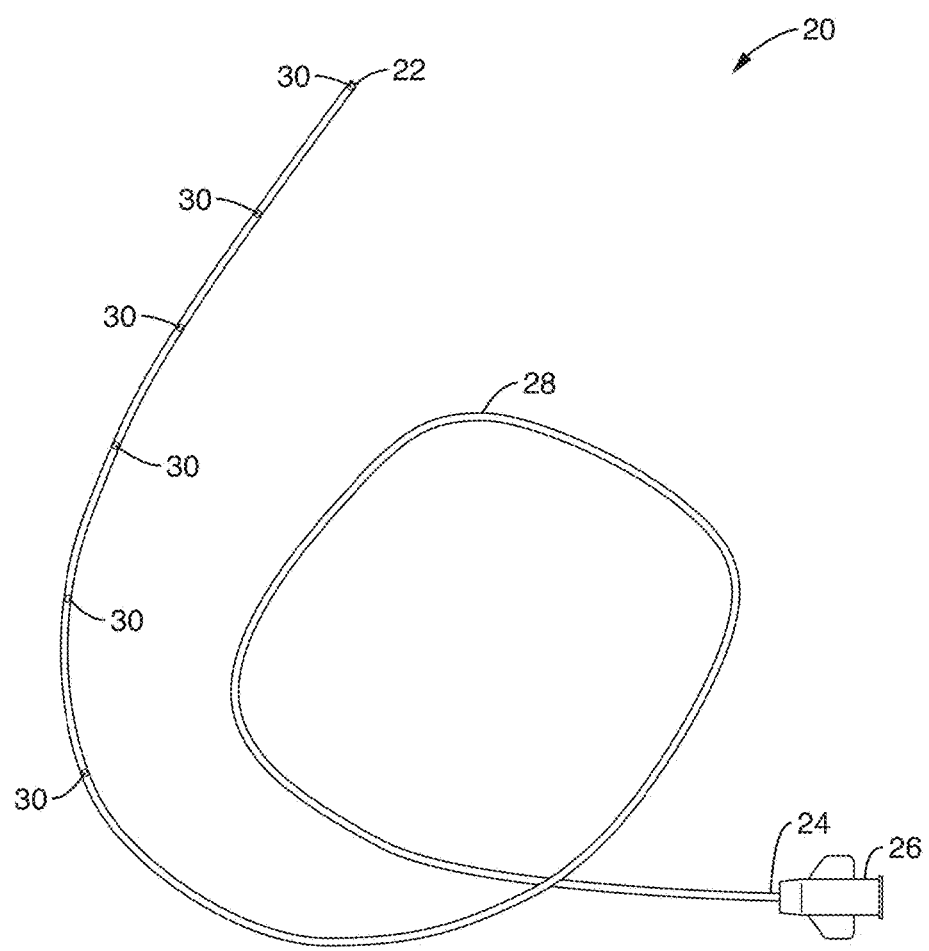
FIG. 2 is a schematic diagram that illustrates an exemplary micro-catheter for precision stent placement in accordance with the present invention.

FIG. 2 illustrates an exemplary micro-catheter 20 for precision stent placement in accordance with the present invention. Micro-catheter 20 comprises a flexible tubular catheter body 28 having an internal passage stemming from distal end 22 to proximal end 24 (at connector 26) for delivery of stents or other instruments/devices to a target location within the body. Starting from the distal end 22 of the catheter body 28, the catheter 20 comprises a plurality (e.g. six) of radio-opaque markers 30 at spaced apart intervals (e.g. 10 mm). The markers 30 act as a ruler to help the physician determine length and location with respect to an internal lumen or vessel.

Markers 30 may comprise any radio opaque material for visibility within the body under x-ray (e.g. radiographic or fluoroscopic imaging). In one embodiment, markers 30 comprise thin-walled tubes placed at spaced-apart locations on catheter body 28, and are typically made from a high density material such as a metal (e.g. platinum, gold or tantalum) for visibility under an x-ray fluoroscope. Markers 30 may be embedded with, or adhered to an outside surface of, catheter body 28. Markers 30 may also comprise a radio-opaque coating deposited on the catheter body.

The radio-opaque markers 30 may be of various quantity, sizes and intervals from the distal end 22 of the catheter body. For example, catheter 20 may comprise a plurality of radio-opaque markers 30 spaced-apart at 5 mm intervals along a distal segment spanning 3 cm-5 cm to provide reference for an operator placing a braided stent. The interval of the radio-opaque markers may range from every 1 mm, 2 mm, 3 mm, 4 mm, and 5 mm or more. The length of the radio-opaque marker segment 30 may be 3 mm, 4 mm, 5 mm, 6 mm, 7 mm, 8 mm, 9 mm, and 10 mm or more to provide sufficient visibility under an x-ray fluoroscope. Each radio-opaque marker 30 may be shaped similarly, or may be variably shaped, e.g. the 5 mm marker (from distal end 22 may comprise one band, the 10 mm marker may comprise 3 bands, the 15 mm marker may comprise 4 bands, and so on.

In one embodiment, the stent delivery catheter 20 may comprise multiple radio-opaque marker bands 30 spaced apart in a 40 mm distal segment 22 at 5 mm intervals, and may be configured for delivery of a 20 mm long braided stent. The stent would generally elongate in the delivery catheter 20 more than twice as much as its unconstrained length. Since the elongated stent in the delivery catheter 20 could not be helpful as a guide to anticipate where the 20 mm long stent ends (when unconstrained), the use of the array of radio-opaque markers 30 would indicate the 20 mm point from the catheter tip, enabling better stent positioning.

Figure 3:
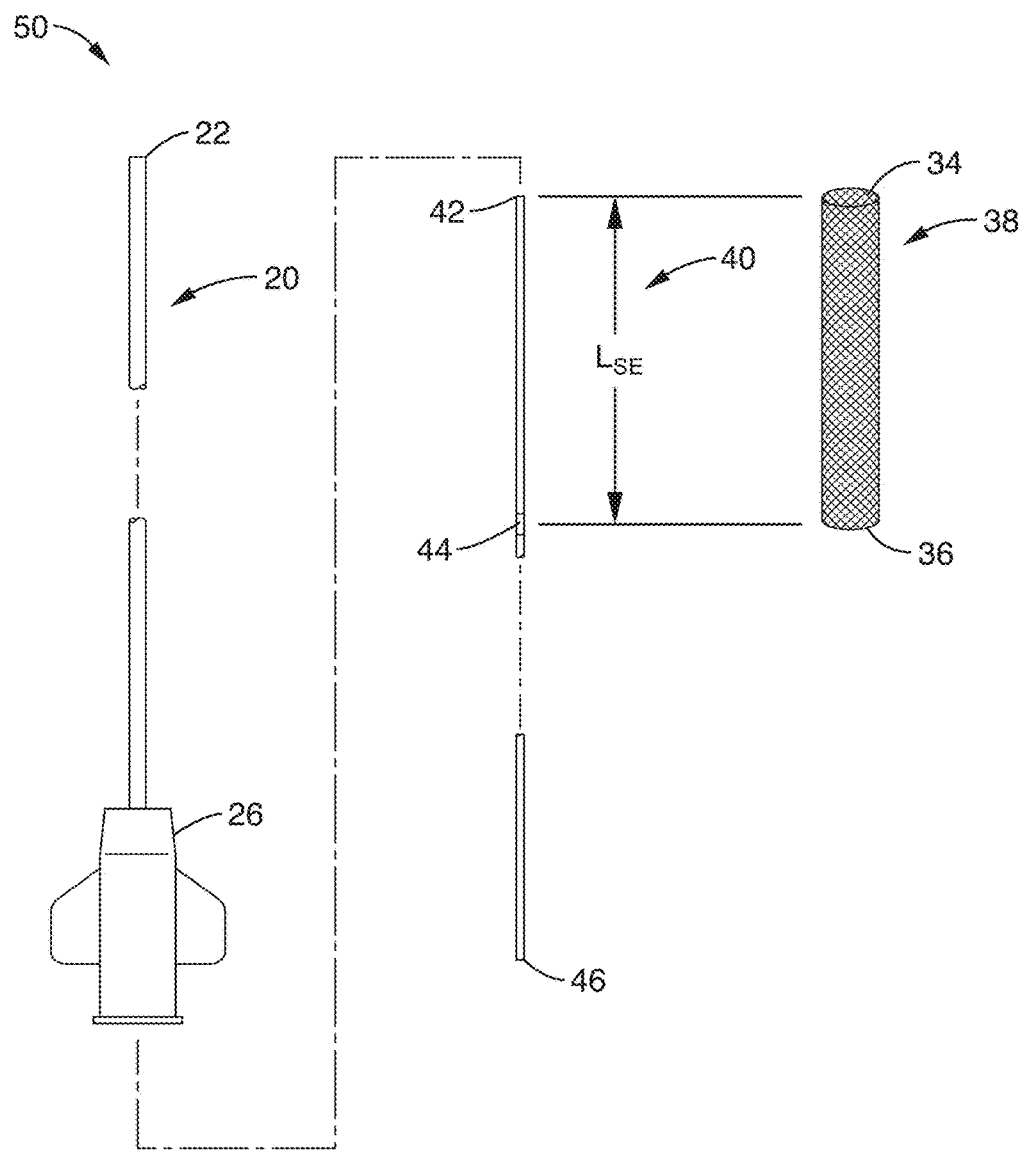
FIG. 3 is a schematic diagram that shows a stent delivery system comprising a stent delivery wire configured for precise stent delivery to a target treatment location within the body.

FIG. 3 shows a stent delivery system 50 comprising a stent delivery wire 40 configured with a proximal end 46 and a distal end 42 for supporting stent 38 for delivery to a target treatment location within the body. The stent 38/delivery wire 40 assembly is delivered through micro catheter 20 (which may comprise radio-opaque markers 30 as shown in FIG. 2) to the target treatment location in the vessel. Once the stent is completely pushed out from the distal end 22 of the delivery catheter 20, it is detached from the delivery wire 40 and is positioned at the target location/lesion permanently.

As shown in FIG. 3, delivery wire 40 comprises a radio-opaque marker 44 a set length $L_{SE}$ from the distal end 42 of the delivery wire. $L_{SE}$ indicates the true, expanded length of the stent 38, i.e. from distal end 34 to proximal end 36. As mentioned previously, stents, and particularly braided stents, are significantly elongated when crimped in a delivery catheter. Radio-opaque marker 44 may comprise a ring or coating of size, shape and composition similar to marker 30 described above for FIG. 2. While delivery wire 40 is typically metallic, it is generally made of stainless steel or Nitinol, and the distal end 42 of the delivery wire is generally very thin so as not to generally be very radio-opaque. Marker 44 generally comprises radio-opaque metal, such as a platinum band, that is welded or bonded on wire 40.

Without the system of the present invention, it is difficult to anticipate where the proximal end 36 of the stent lands in relation to the target anatomy. Using system 50 of the present invention, the physician may use the radio-opaque marker 44 on the delivery wire 40 to give an indication where the proximal end 36 of the unconstrained stent 38 would land after delivery through the micro catheter 20, and thus start extraction of the distal end 34 of stent 38 at the appropriate distance from the target anatomy. For example, a 20 mm long braided stent 38 is crimped and mounted on delivery wire 40 having a radio-opaque marker positioned on the wire at a point that indicates $L_{SE}$=20 mm from the distal tip 34 of the stent 38 (which may or may not correspond to the distance from distal end 42 of the wire 40). With this marker 44, the operator can easily anticipate where the proximal end 36 of the stent would land in the tortuous vessel, and select a delivery location of the stent 38 (generally starting at the distal end 22 of the micro-catheter) that corresponds to the desired treatment location (e.g. the aneurysm 52).

Figure 4:
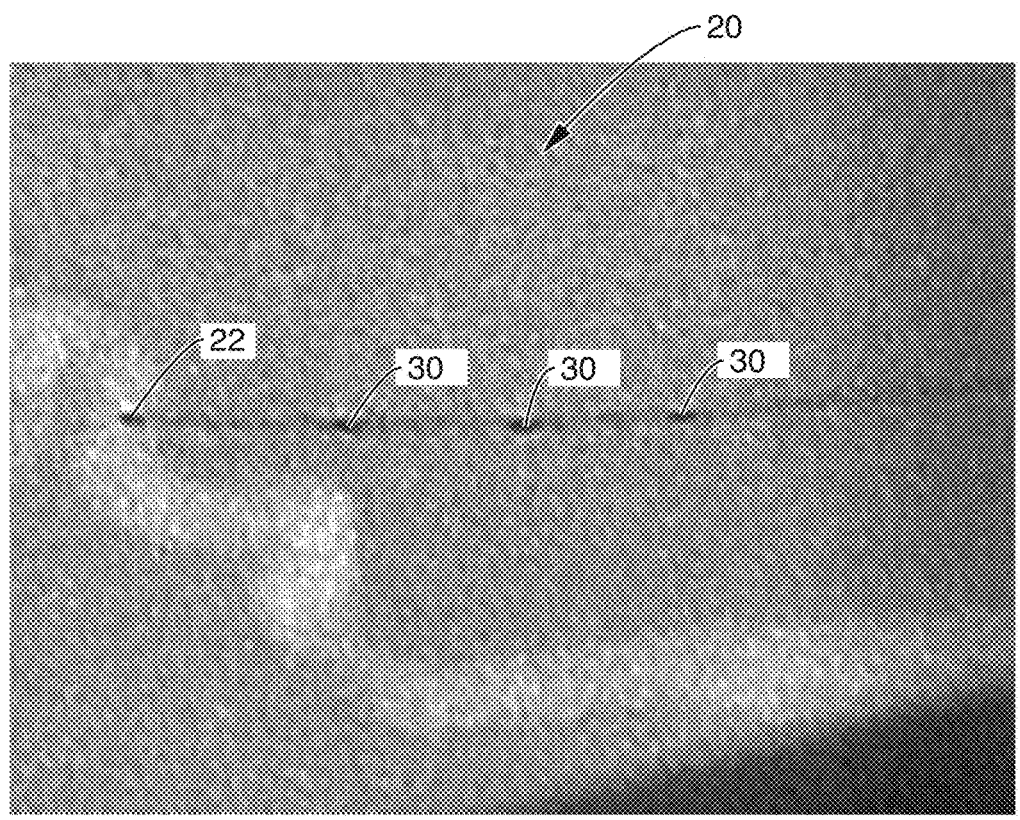
FIG. 4 is an exemplary radiographic image that shows a micro-catheter comprising multiple radio-opaque maker bands at 10 mm intervals in use within tissue in accordance with the present invention.

FIG. 4 shows an exemplary radiographic image of the catheter 20 comprising multiple radio-opaque maker bands 30 at 10 mm intervals in use within tissue in accordance with the present invention. As seen in FIG. 4, the markers 30 are clearly delineated, and provide valuable visualization as a position indicator when placed in a tortuous anatomy.

Figure 5:
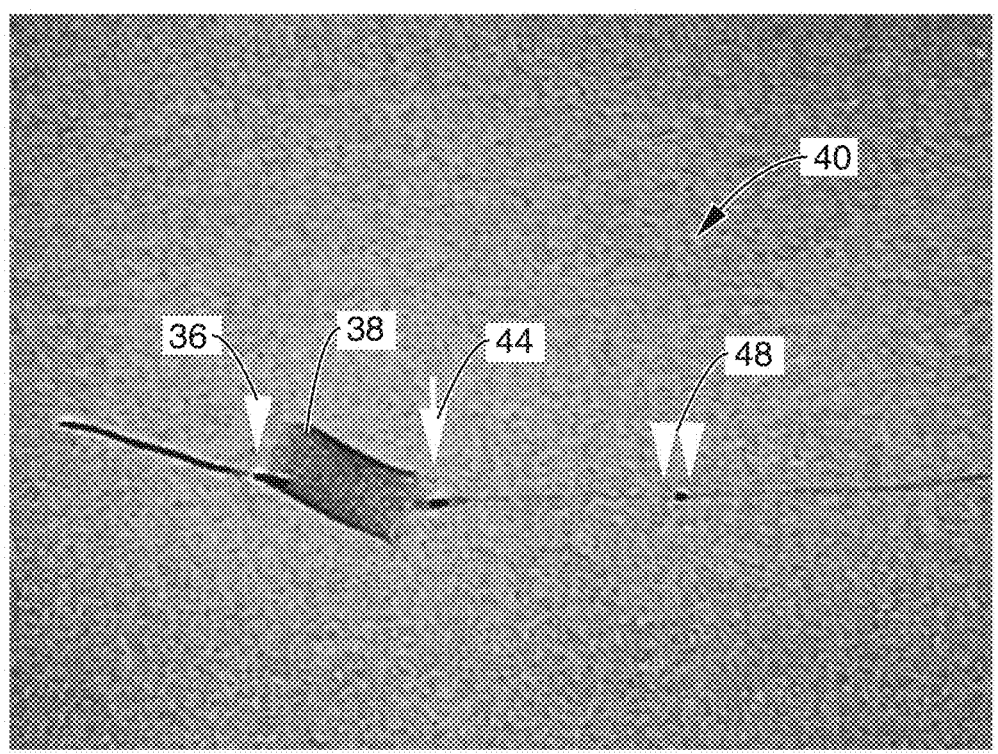
FIG. 5 is a radiographic image of an expanded stent and stent delivery wire with radio-opaque markers in accordance with the present invention.

FIG. 5 shows a radiographic image of an expanded stent 38 and stent delivery wire 40 with radio-opaque markers for illustrating expanded and compressed lengths. The image shows a braided stent 38 after it is delivered, but still attached to the delivery wire 40. The left-most arrowhead shows a maker on the delivery wire 40 that corresponds to the distal end 36 of the stent 38. The middle arrow indicates an additional radio-opaque marker 44 that represents the unconstrained length (or location of proximal end 36 when unconstrained) of the stent 38. The double arrowheads 48 correspond to the location of the proximal end 36 of the stent 38 when crimped and constrained in the catheter 20 or delivery sheath. The marker 44 therefore guides the treating physician to better anticipate where the proximal end 36 of the stent lands.

Figure 6:
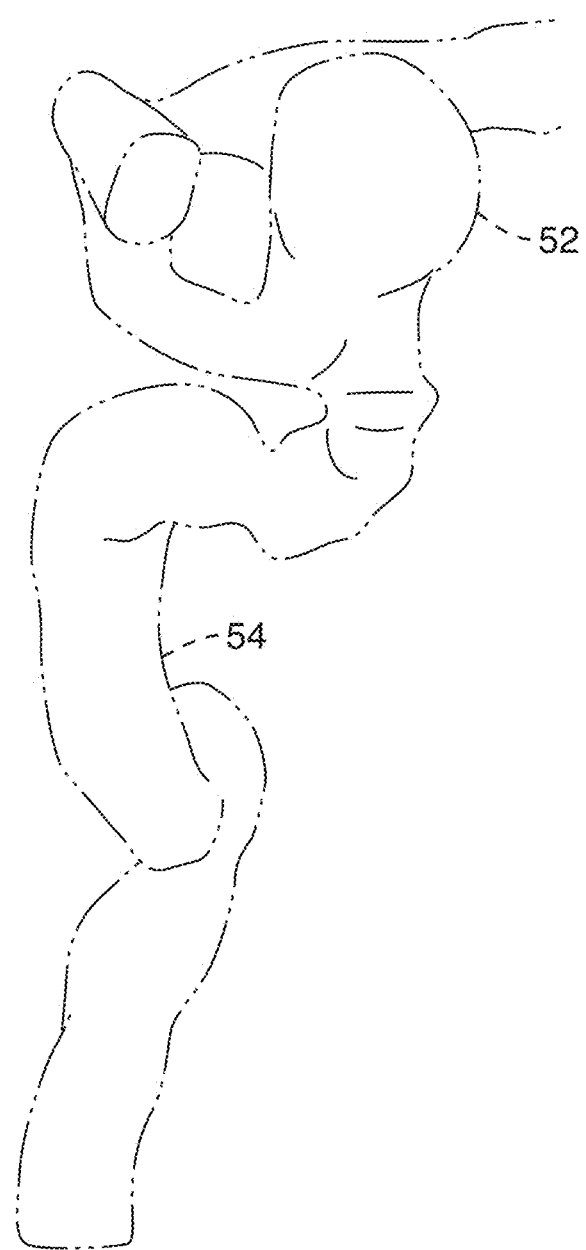
FIG. 6 is a schematic diagram of a brain artery (e.g. left internal carotid artery) and a brain aneurysm as the target treatment anatomy.

FIG. 6 illustrates a schematic diagram of a brain artery 54 (e.g. left internal carotid artery) and a brain aneurysm 52 as the target treatment anatomy. FIG. 7 through FIG. 10 show a first embodiment of the invention of a stent delivery procedure using the micro-catheter 20 illustrated in FIG. 2. FIG. 11 through FIG. 14 show a second embodiment of the invention of a stent delivery procedure using the stent delivery system 50 illustrated in FIG. 3.

Figure 7:
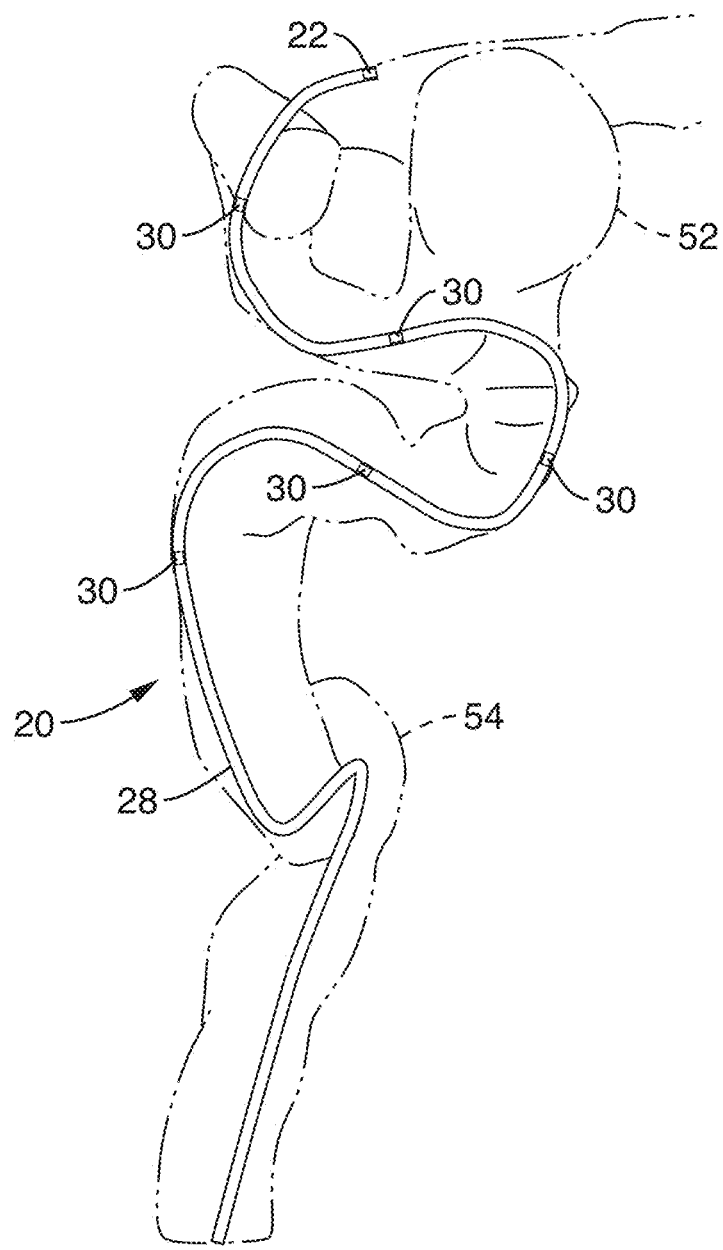
FIG. 7 is a schematic diagram of the micro-catheter of FIG. 2 with radio-opaque markers navigated into the brain artery of FIG. 6.

FIG. 7 illustrates a schematic diagram of the micro-catheter 20 with radio-opaque markers 30 navigated into the brain artery 54 and is placed across the aneurysm 52 neck. The general strategy is to cover the aneurysm 52 neck with a stent. As shown in FIG. 7, the distal end 22 of the micro-catheter 20 is delivered past the target location 52 and is placed at a location corresponding to the desired extraction of the stent 38 (e.g. where the distal end 34 of the stent will be located at distal end 22).

Figure 8:
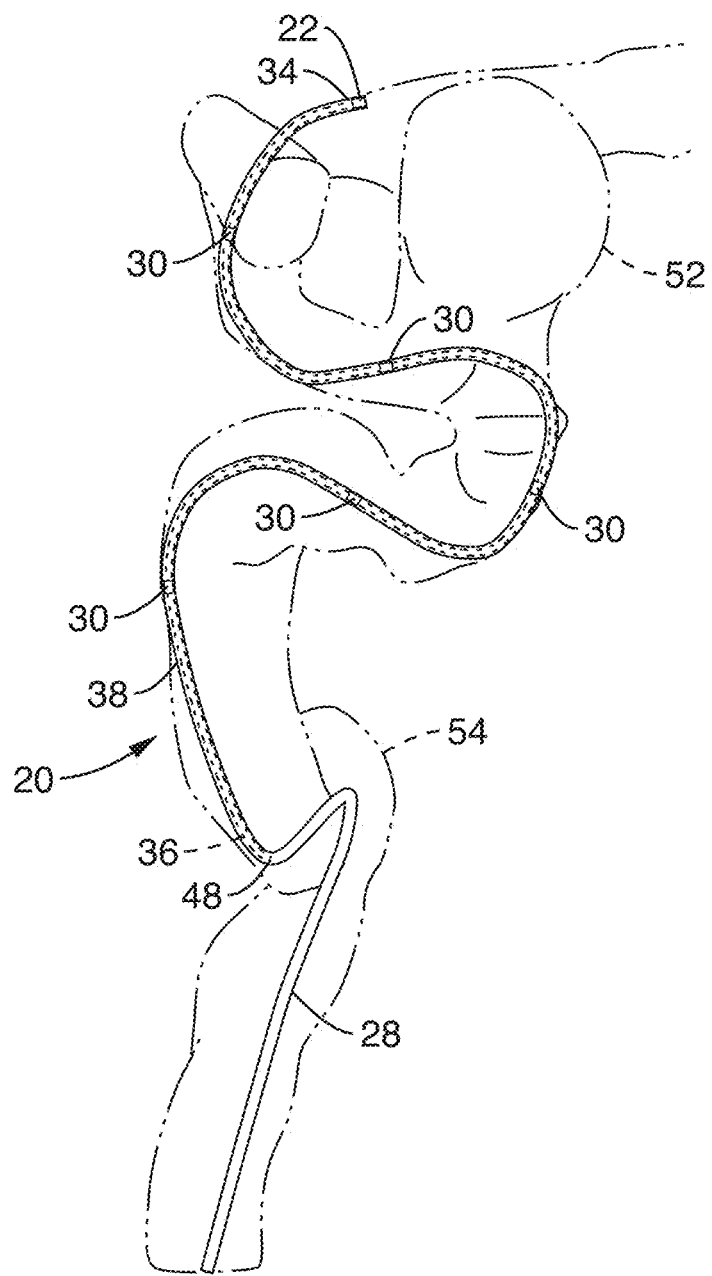
FIG. 8 is a schematic diagram of a braided aneurysm stent inserted into the micro-catheter of FIG. 7.

FIG. 8 illustrates a schematic diagram of a braided aneurysm stent 38 (e.g. 30 mm length) inserted into the micro-catheter 20. In general, stents are very radio-opaque so that the entire length is clearly visible even if it is in a micro-catheter 20. Due to the significant elongation, the 30 mm stent is much longer than the true length. This elongation on top of the tortuous anatomy sometimes poses a challenge to the physician for accurate placement. The multiple radio-opaque markers 30 at known intervals on the micro-catheter 20 allow the physician to ignore the elongation and simply use the 30 mm point marker (e.g. $3^{rd}$ marker from distal end 22 at 10 mm spacing) as a reference. If the stent 38 lands in the vessel 54 as projected, it will span the neck of the aneurism 52.

Figure 9:
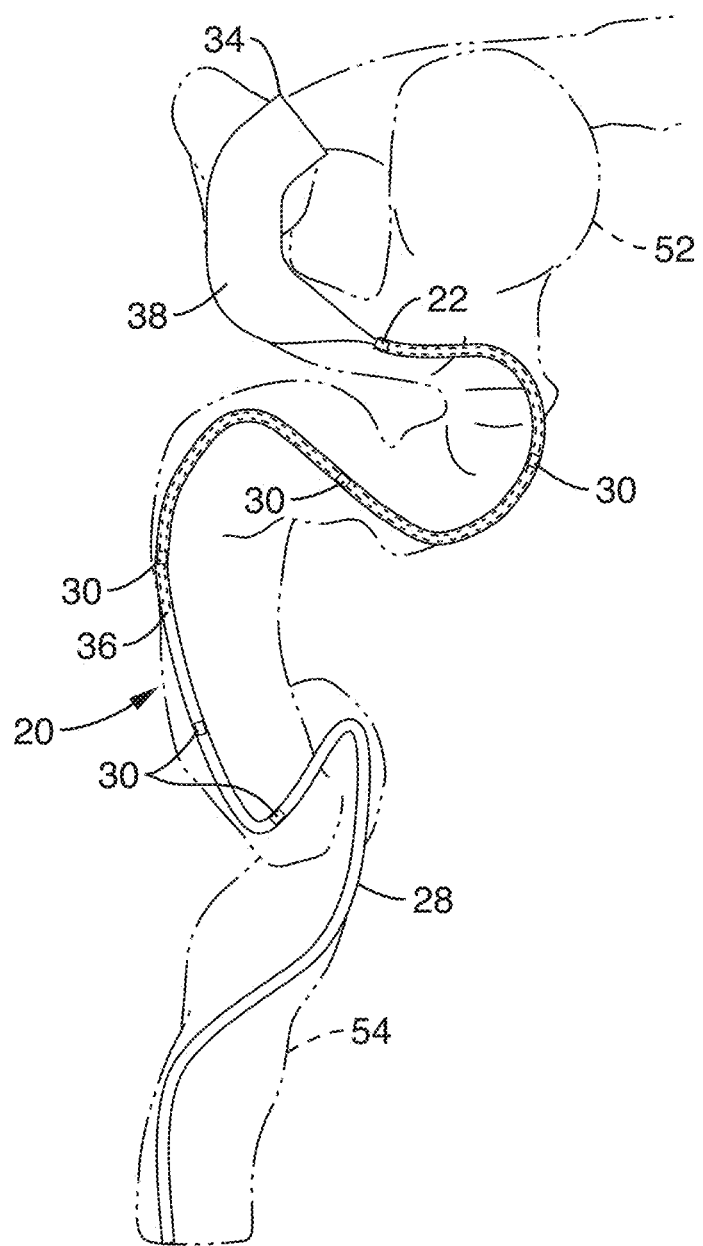
FIG. 9 is a schematic diagram of the micro-catheter of FIG. 8 being pulled back as the stent is being pushed out of the distal end.

FIG. 9 illustrates a schematic diagram of the micro-catheter 20 being pulled back as stent 38 is being pushed out of the distal end 22. Distal end 34 of the stent lands at the location of the distal end 22 at extraction, while proximal end 36 is still within the micro-catheter 20 as distal end 22 of the micro-catheter is pulled back to the location of the aneurysm 52. Due to the stent elongation effect in the micro-catheter 20, the remaining length of the stent 38 in the micro-catheter is significantly different from the length that the stent 38 covers within the artery 54.

Figure 10:
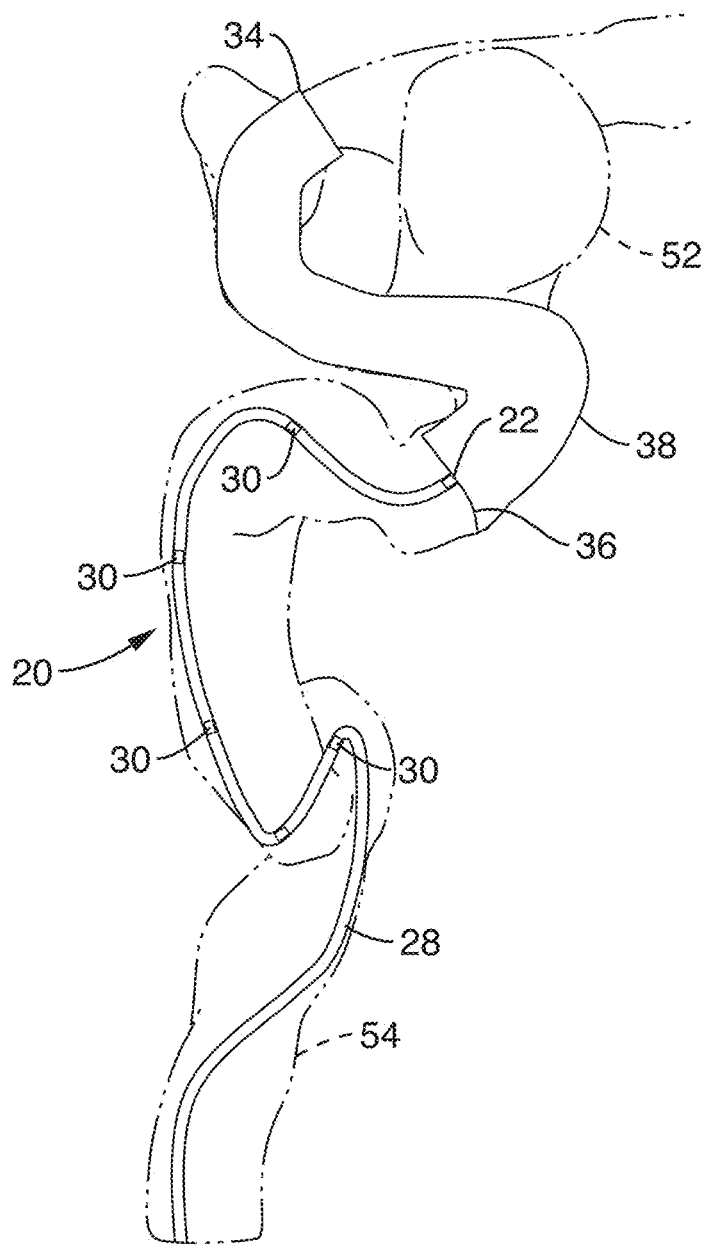
FIG. 10 is a schematic diagram of the stent of FIG. 9 completely extracted from the micro-catheter for completion of the stent placement.

FIG. 10 illustrates a schematic diagram of the stent 38 completely extracted from the micro-catheter 20 for completion of the stent placement. The proximal end 36 of the stent 38 lands well beyond the aneurysm 52 neck to fully cover or occlude the target lesion.

Figure 11:
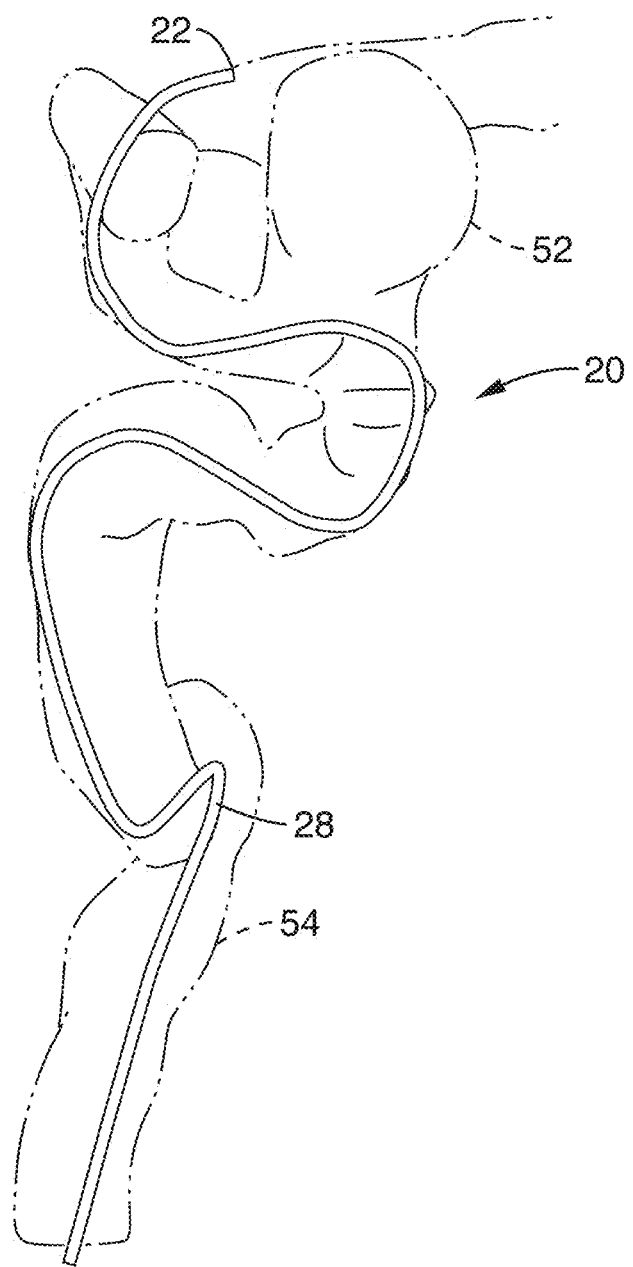
FIG. 11 is a schematic diagram of a stent delivery micro-catheter navigated into the brain artery of FIG. 6.

FIG. 11 illustrates a schematic diagram of a stent delivery micro-catheter 20 navigated into the brain artery and placed across the aneurysm neck. In this configuration, delivery micro-catheter 20 does not have radio-opaque markers 30 as shown in FIG. 2. However, it is contemplated that markers 30 may also be employed. As with the previous procedure described in FIG. 7 through FIG. 10, the desired treatment plan is to cover the aneurysm neck 52 with a stent (e.g. 30 mm length).

Figure 12:
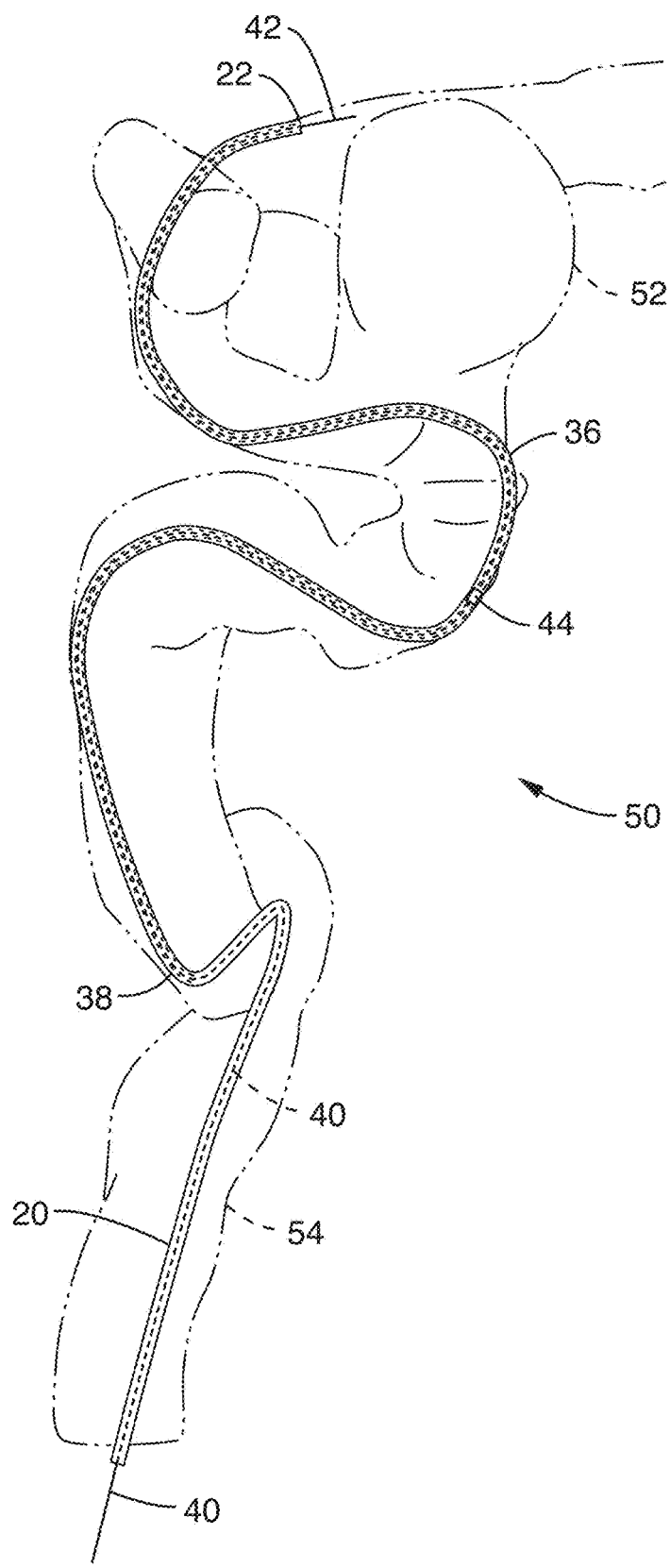
FIG. 12 is a schematic diagram of a braided aneurysm stent inserted into the micro-catheter of FIG. 11 over a delivery wire.

FIG. 12 illustrates a schematic diagram of a braided aneurysm stent 38 (e.g. 30 mm) inserted into the micro-catheter 20 over a delivery wire 40 so that the distal end 42 of the delivery wire is at or past the distal opening 22 of the micro-catheter 20. In general, stents are very radio-opaque so that the entire length is clearly visible even it is in a micro-catheter 20. Due to the significant elongation, the 30 mm stent 38 is much longer than the true length. This elongation on top of the tortuous anatomy sometimes poses a challenge to the physician for accurate placement. The radio-opaque marker 44 at known distance $L_{SE}$ on the delivery wire 40 allows the physician to ignore the elongation and simply use the point marker 44 (e.g. 30 mm from the distal end 34 of the stent 38 when positioned on the delivery wire 40) as a reference. Having the radio-opaque marker 44 that indicates the unconstrained length of the stent 38, the physician can simply navigate the stent delivery system (e.g. distal end 22 of micro-catheter 20) to the point where the desired stent placement starts in light of the radio-opaque marker 44 that indicates where the proximal end 36 of the stent 38 should land.

Figure 13:
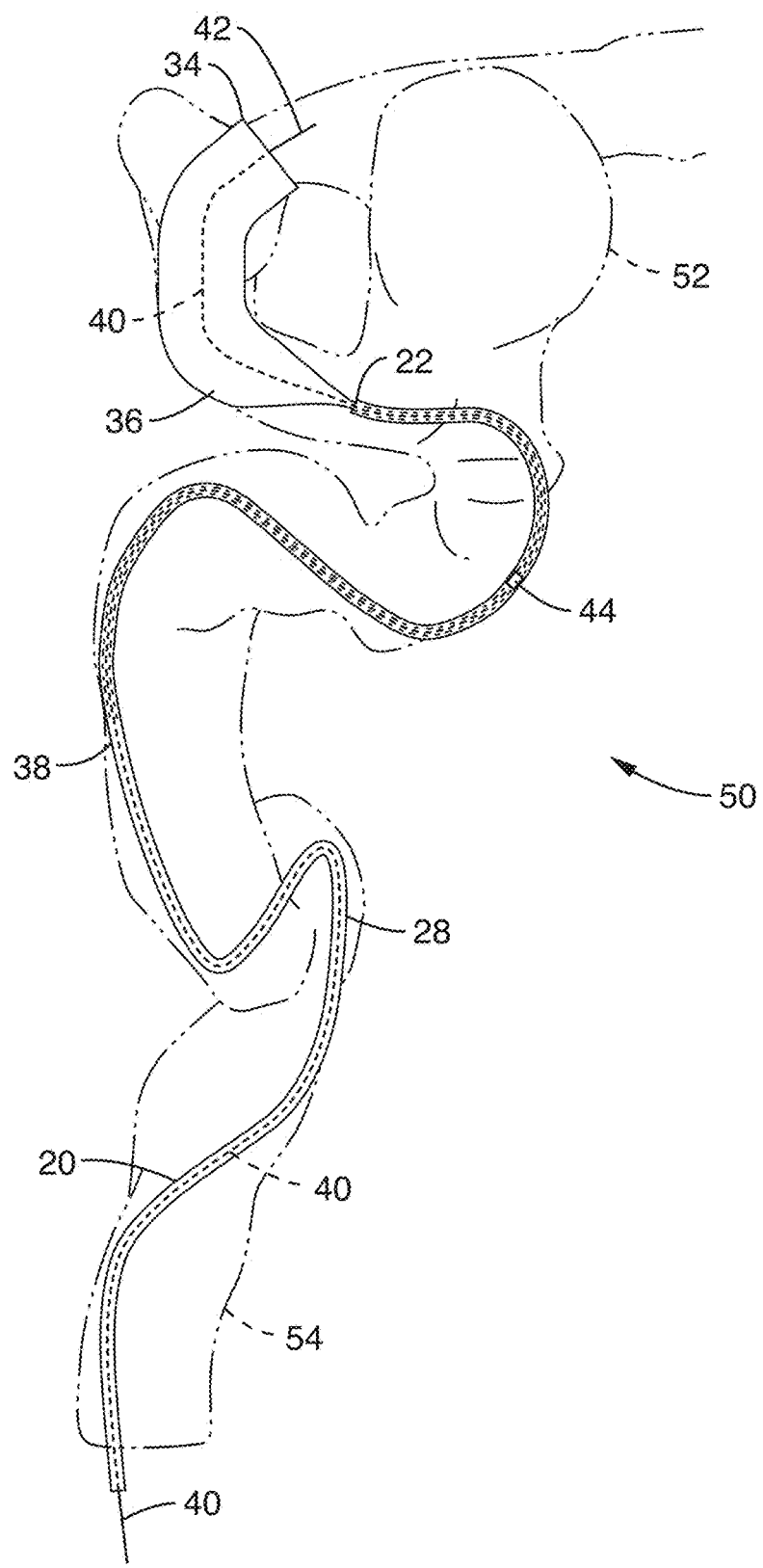
FIG. 13 is a schematic diagram of the micro-catheter of FIG. 12 being pulled back as the stent and delivery wire assembly are being pushed out of the distal end.

FIG. 13 illustrates a schematic diagram of the micro-catheter 20 being pulled back as stent 38 and delivery wire 40 are being pushed out of the distal end 22. Distal end 34 of the stent 38 lands at the location of the distal end 22 at extraction, while proximal end 36 is still within the micro-catheter 20 as distal end 22 of the micro-catheter is pulled back to the location of the aneurysm 52. Due to the stent elongation effect in the micro-catheter 20, the remaining length of the stent 38 in the micro-catheter is significantly different from the length that the stent 38 covers within the artery 54. Nevertheless, the physician can use the radio-opaque marker 44 as a predicted stent 38 ending point.

Figure 14:
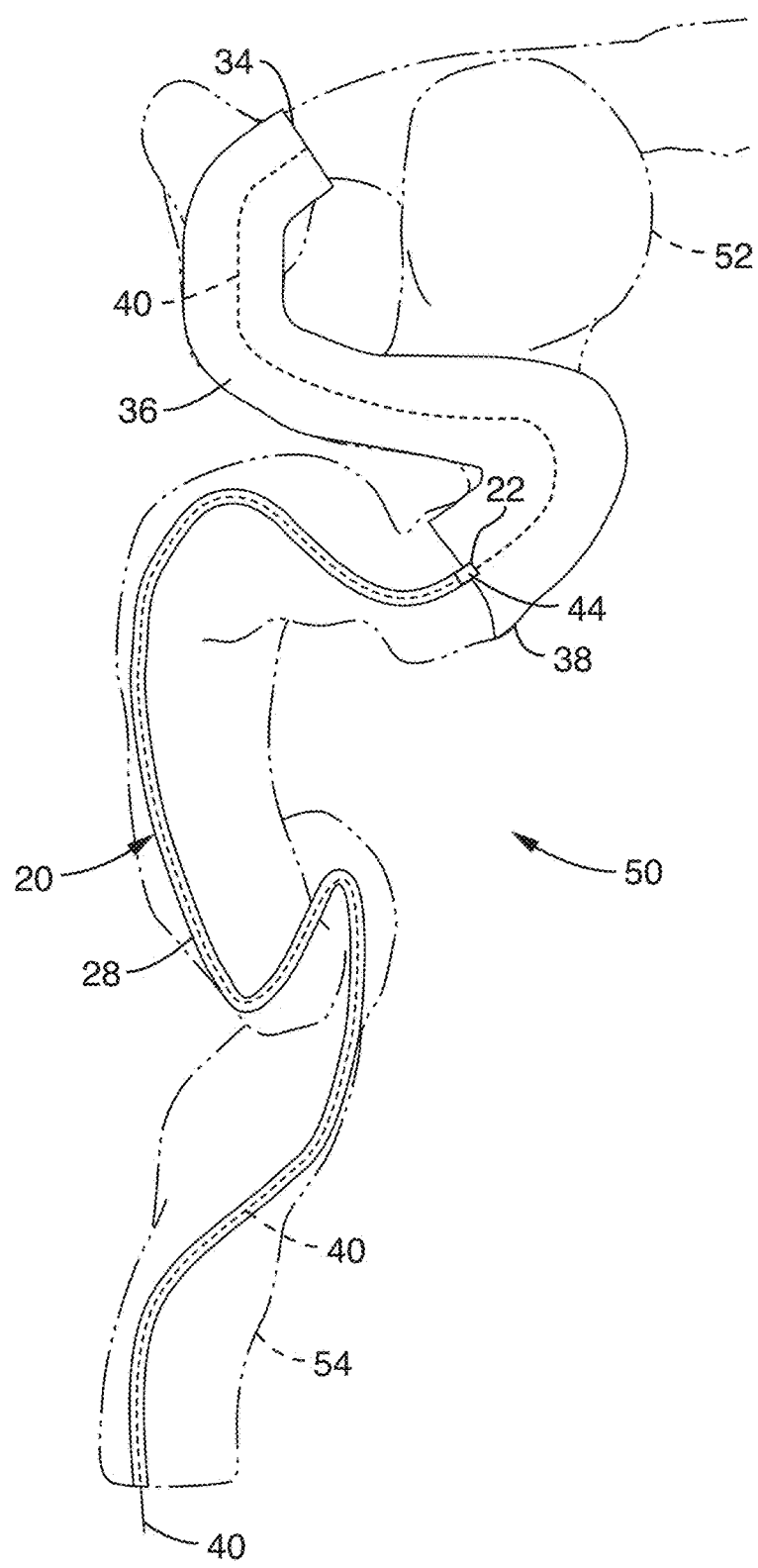
FIG. 14 is a schematic diagram of the stent and delivery wire assembly of FIG. 13 completely extracted from the micro-catheter for completion of the stent placement.

FIG. 14 illustrates a schematic diagram of the stent 38 and delivery wire 40 assembly completely extracted from the micro-catheter 20 for completion of the stent placement. The proximal end 36 of the stent 38 lands well beyond the aneurysm 52 neck at the projected marker location 44 on the delivery wire 40 to fully cover or occlude the target lesion 52.

While the above examples are illustrated with use of a braided stent because of its associated substantial foreshortening, it is appreciated that the systems and methods of the present invention may be used with stents fabricated via any method, including micro-machined metal stents fabricated with laser-machining, photo-etching, electroforming, and micro-electro-discharge machining, and polymeric stents fabricated using injection, compression, or fused deposition molding processes.

It is appreciated that the length of the stent 38 while in a completely unconstrained state may be different than (e.g. smaller) the length of the stent when "unconstrained" in the lumen 54 outside of delivery micro-catheter 20. For example, a stent may be sized to have a diameter that compresses against the inner wall of the lumen 54. Thus, the lumen 54 may have a constraining effect on the stent 38 that causes it to be slightly larger than when in completely free state outside the body. Thus, length $L_{SE}$ of the marker location in FIG. 3, and the incremental spacing between markers 30 in micro catheter 20 of FIG. 2, may have dimensions that are larger than the unconstrained length of the stent 38.

From the discussion above it will be appreciated that the invention can be embodied in various ways, including the following:

1. An apparatus for precision delivery of a stent within a lumen of the body, comprising: a delivery wire having a proximal end and a distal end; wherein the distal end of the delivery wire is configured to support an expandable stent in a compressed, elongated configuration; wherein the delivery wire comprises a radio-opaque marker disposed at a predetermined distance from the distal end of the delivery wire; and wherein the predetermined distance corresponds to a length of the stent when the stent is in a shortened, unconstrained state.

2. An apparatus as in any of the previous embodiments: wherein the predetermined distance corresponds to a length of a braided stent in a shortened, unconstrained state; and wherein the length of the braided stent in a shortened, unconstrained state is smaller than the length of the braided stent when in a constrained state within a catheter.

3. An apparatus as in any of the previous embodiments: wherein the predetermined distance corresponds to a length of a micro-machined stent in a shortened, unconstrained state; and wherein the length of the micro-machined stent in a shortened, unconstrained state is smaller than the length of the braided stent when in a constrained state within a catheter.

4. An apparatus as in any of the previous embodiments: wherein the delivery wire and stent are configured to be delivered through a catheter in the compressed, elongated configuration to a treatment location within the lumen.

5. An apparatus as in any of the previous embodiments; wherein the treatment location comprises an aneurysm within a cerebral blood vessel; and wherein the stent is configured to span across the aneurysm when disposed at the treatment location in the unconstrained state.

6. An apparatus for precision delivery of a stent within a lumen of the body, comprising: a micro-catheter having a proximal end and a distal end; wherein the micro-catheter is configured to house an expandable stent in a compressed, elongated configuration for delivery to a treatment location within the lumen; and wherein the micro-catheter comprises three or more radio-opaque markers disposed at spaced-apart intervals from the distal end of the micro-catheter.

7. An apparatus as in any of the previous embodiments, wherein the spaced-apart marker intervals correspond to a length of the stent when the stent is in a shortened, unconstrained state.

8. An apparatus as in any of the previous embodiments, wherein the spaced-apart marker intervals form a ruler visible under radiographic imaging.

9. An apparatus as in any of the previous embodiments: wherein the spaced-apart intervals correspond to a length of a braided stent in a shortened, unconstrained state; and wherein the length of the braided stent in a shortened, unconstrained state is smaller than the length of the braided stent when in a constrained state within the micro-catheter.

10. An apparatus as in any of the previous embodiments: wherein the predetermined distance corresponds to a length of a micro-machined stent in a shortened, unconstrained state; and wherein the length of the micro-machined stent in a shortened, unconstrained state is smaller than the length of the braided stent when in a constrained state within the micro-catheter.

11. An apparatus as in any of the previous embodiments: wherein the micro-catheter is sized to allow delivery of the stent through the micro-catheter in the compressed, elongated configuration to the treatment location within the lumen.

12. An apparatus as in any of the previous embodiments: wherein the treatment location comprises an aneurysm within a cerebral blood vessel; and wherein the stent is configured to span across the aneurysm when disposed at the treatment location in the unconstrained state.

13. A system for precision delivery of a stent within a lumen of the body, comprising: a delivery wire having a proximal end and a distal end; wherein the distal end of the delivery wire is configured to support an expandable stent in a compressed, elongated configuration; a micro-catheter having a proximal end and a distal end; wherein the micro-catheter is configured to house the expandable stent while in the compressed, elongated configuration on the delivery wire for delivery to a treatment location within the lumen; wherein the delivery wire comprises a radio-opaque marker disposed at a predetermined distance from the distal end of the delivery wire; and wherein the predetermined distance corresponds to a length of the stent when the stent is in a shortened, unconstrained state.

14. A system as in any of the previous embodiments: wherein the predetermined distance corresponds to a length of a braided stent in a shortened, unconstrained state; and wherein the length of the braided stent in a shortened, unconstrained state is smaller than the length of the braided stent when in a constrained state within the micro-catheter.

15. A system as in any of the previous embodiments: wherein the predetermined distance corresponds to a length of a micro-machined stent in a shortened, unconstrained state; and wherein the length of the micro-machined stent in a shortened, unconstrained state is smaller than the length of the braided stent when in a constrained state within the micro-catheter.

16. A system as in any of the previous embodiments: wherein the treatment location comprises an aneurysm within a cerebral blood vessel; and wherein the stent is configured to span across the aneurysm when disposed at the treatment location in the unconstrained state.

17. A system as in any of the previous embodiments, wherein the micro-catheter comprises a plurality of radio-opaque markers disposed at spaced-apart intervals from the distal end of the micro-catheter to form a ruler visible under radiographic imaging.

18. A method for precision delivery of a stent within a lumen of the body, comprising: positioning a distal end of a micro-catheter to a treatment location within the lumen; delivering an expandable stent in a compressed, elongated configuration on a distal end of a delivery wire through the micro-catheter to the distal end of the micro-catheter; wherein the delivery wire comprises a radio-opaque marker disposed at a predetermined distance from the distal end of the delivery wire; and wherein the predetermined distance corresponds to a length of the stent when the stent is in a shortened, unconstrained state; locating the distal end of the micro-catheter at a delivery location corresponding to the radio-opaque marker and the treatment location; and extracting the stent from the distal end of the micro-catheter at the delivery location.

19. A method as in any of the previous embodiments: wherein the predetermined distance corresponds to a length of a braided stent in a shortened, unconstrained state; and wherein the length of the braided stent in a shortened, unconstrained state is smaller than the length of the braided stent when in a constrained state within the micro-catheter.

20. A method as in any of the previous embodiments: wherein the treatment location comprises an aneurysm within a cerebral blood vessel; and wherein the delivery location is selected such that the stent spans across the aneurysm when disposed at the treatment location in the unconstrained state.

21. A method for precision delivery of a stent within a lumen of the body, comprising: positioning a distal end of a micro-catheter to a treatment location within the lumen; delivering an expandable stent in a compressed, elongated configuration through the micro-catheter to the distal end of the micro-catheter; wherein the micro-catheter comprises three or more radio-opaque markers disposed at spaced-apart intervals from the distal end of the micro-catheter; and locating the distal end of the micro-catheter at a delivery location corresponding to the radio-opaque marker and the treatment location; and extracting the stent from the distal end of the micro-catheter at the delivery location.

22. A method as in any of the previous embodiments, wherein the spaced-apart marker intervals correspond to a length of the stent when the stent is in a shortened, unconstrained state.

23. A method as in any of the previous embodiments, wherein the spaced-apart marker intervals form a ruler visible under radiographic imaging.

24. A method as in any of the previous embodiments: wherein the spaced-apart intervals correspond to a length of a braided stent in a shortened, unconstrained state; and wherein the length of the braided stent in a shortened, unconstrained state is smaller than the length of the braided stent when in a constrained state within the micro-catheter.

25. A method as in any of the previous embodiments: wherein the spaced-apart intervals corresponds to a length of a micro-machined stent in a shortened, unconstrained state; and wherein the length of the micro-machined stent in a shortened, unconstrained state is smaller than the length of the braided stent when in a constrained state within the micro-catheter.

26. A method as in any of the previous embodiments: wherein the micro-catheter is sized to allow delivery of the stent through the micro-catheter in the compressed, elongated configuration to the treatment location within the lumen.

27. A method as in any of the previous embodiments: wherein the treatment location comprises an aneurysm within a cerebral blood vessel; and wherein the delivery location is selected such that the stent spans across the aneurysm when disposed at the treatment location in the unconstrained state.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for precision delivery of a stent within a lumen of the body, comprising:
    an expandable stent having a proximal end and a distal end defining a stent length there between;
    wherein the expandable stent comprises a compressed, elongated configuration having a compressed stent length that is longer than an unconstrained stent length when the expandable stent is in a shortened, unconstrained state;
    a delivery wire having a proximal end and a terminal distal end; wherein a distal portion of the delivery wire is configured to support the expandable stent in the compressed, elongated configuration for delivery to a treatment location within the lumen;
    wherein the delivery wire comprises a radio-opaque marker disposed at a predetermined distance from the terminal distal end of the delivery wire;
    wherein the radio-opaque marker is positioned such that the stent, when disposed on the distal portion of the delivery wire in the compressed, elongated configuration, has at least a portion extending proximal to the radio-opaque marker and is able to move freely past the radio-opaque marker along the delivery wire to be deployed in the lumen;
    and wherein the predetermined distance matches the unconstrained stent length of the expandable stent so as to indicate a proximal end location of the stent when the stent is delivered to the treatment location in the shortened, unconstrained state.

2. An apparatus as recited in claim 1, wherein the expandable stent comprises a braided stent;
    wherein the predetermined distance matches the unconstrained stent length of the braided stent so as to indicate a proximal end location of the braided stent in the shortened, unconstrained state.

3. An apparatus as recited in claim 1, wherein the expandable stent comprises a micro-machined stent; wherein the predetermined distance matches the unconstrained stent length of the micro-machined stent so as to indicate a proximal end location of the micro-machined stent in the shortened, unconstrained state.

4. An apparatus as recited in claim 1, wherein the delivery wire and the stent are configured to be delivered through a catheter in the compressed, elongated configuration to the treatment location within the lumen.

5. An apparatus as recited in claim 1, wherein the delivery wire and stent are configured to be delivered to a treatment location comprising an aneurysm within a cerebral blood vessel; and wherein the stent is configured to span across the aneurysm when disposed at the treatment location in the unconstrained state.

6. An apparatus for precision delivery of a stent within a lumen of the body, comprising:
an expandable stent having a proximal end and a distal end defining a stent length there between;
wherein the expandable stent comprises a compressed, elongated configuration having a compressed stent length that is longer than an unconstrained stent length when the expandable stent is in a shortened, unconstrained state;
a micro-catheter having a proximal end and a terminal distal end; wherein the micro-catheter is configured to house the expandable stent in the compressed, elongated configuration for delivery to a treatment location within the lumen;
and wherein the micro-catheter comprises three or more radio-opaque markers disposed at spaced-apart intervals from the terminal distal end of the micro-catheter; wherein the radio-opaque markers are positioned such that the stent, when disposed within the micro-catheter in the compressed, elongated configuration, has at least a portion extending proximal to the radio-opaque markers and is able to move freely past the radio-opaque markers along the micro-catheter to be deployed in the lumen; and
wherein the three or more radio-opaque markers comprise a first marker positioned a distance from the terminal distal end of the micro-catheter that matches the unconstrained stent length, a remainder of the three or more radio-opaque markers being positioned at said spaced-apart marker intervals, wherein the first marker indicates a proximal end location of the stent when the stent is delivered to the treatment location in the shortened, unconstrained state after exiting the terminal distal end of the micro-catheter.

7. An apparatus as recited in claim 6, wherein the spaced-apart marker intervals form a ruler visible under radiographic imaging.

8. An apparatus as recited in claim 6, wherein the expandable stent comprises a braided stent; and wherein the distance from the distal end of the micro-catheter to the first marker matches the unconstrained stent length of the braided stent so as to indicate a proximal end location of the braided stent in the shortened, unconstrained state.

9. An apparatus as recited in claim 6, wherein the expandable stent comprises a micro-machined stent; and wherein the distance from the distal end of the micro-catheter to the first marker matches the unconstrained stent length of the braided stent so as to indicate a proximal end location of the micro-machined stent in the shortened, unconstrained state.

10. An apparatus as recited in claim 6, wherein the micro-catheter is sized to allow delivery of the stent through the micro-catheter in the compressed, elongated configuration to the treatment location within the lumen.

11. An apparatus as recited in claim 10, wherein the micro-catheter and the stent are configured to be delivered to the treatment location, wherein the treatment location comprises an aneurysm within a cerebral blood vessel; and wherein the stent is configured to span across the aneurysm when disposed at the treatment location in the unconstrained state.

12. A system for precision delivery of a stent within a lumen of the body, comprising:
an expandable stent having a proximal end and a distal end defining a stent length there between;
wherein the expandable stent comprises a compressed, elongated configuration having a compressed stent length that is longer than an unconstrained stent length when the expandable stent is in a shortened, unconstrained state;
a delivery wire having a proximal end and a terminal distal end;
wherein a distal portion of the delivery wire is configured to support the expandable stent in the compressed, elongated configuration;
a micro-catheter having a proximal end and a distal end;
wherein the micro-catheter is configured to house the expandable stent while in the compressed, elongated configuration on the delivery wire for delivery to a treatment location within the lumen;
wherein the delivery wire comprises a radio-opaque marker disposed at a predetermined distance from the terminal distal end of the delivery wire;
wherein the radio-opaque marker is positioned such that the stent, when disposed on the distal portion of the delivery wire in the compressed, elongated configuration, has at least a portion extending proximal to the radio-opaque marker and is able to move freely past the radio-opaque marker along the delivery wire to be deployed in the lumen;
and wherein the predetermined distance matches the unconstrained stent length of the expandable stent so as to indicate a proximal end location of the stent when the stent is delivered to the treatment location in the shortened, unconstrained state.

13. A system as recited in claim 12, wherein the expandable stent comprises a braided stent; wherein the predetermined distance matches the unconstrained stent length of the braided stent so as to indicate a proximal end location of the braided stent in the shortened, unconstrained state.

14. A system as recited in claim 12, wherein the expandable stent comprises a micro-machined stent; wherein the predetermined distance matches the unconstrained stent length of the micro-machined stent so as to indicate a proximal end location of the micro-machined stent in the shortened, unconstrained state.

15. A system as recited in claim 12, wherein the delivery wire and the stent are configured to be delivered to the treatment location, wherein the treatment locations comprises an aneurysm within a cerebral blood vessel; and wherein the stent is configured to span across the aneurysm when disposed at the treatment location in the unconstrained state.

16. A system as recited in claim 12, wherein the micro-catheter comprises a plurality of radio-opaque markers disposed at spaced-apart intervals from the distal end of the micro-catheter to form a ruler visible under radiographic imaging.

17. A method for precision delivery of a stent within a lumen of the body, comprising:
  positioning a terminal distal end of a micro-catheter to a treatment location within the lumen;
  delivering an expandable stent in a compressed, elongated configuration on a distal portion of a delivery wire through the micro-catheter to the terminal distal end of the micro-catheter, wherein the expandable stent comprises a shortened, unconstrained state having an unconstrained stent length that is shorter than a compressed stent length when the stent is in a compressed, elongated configuration;
  wherein the delivery wire comprises a radio-opaque marker disposed at a predetermined distance from a terminal distal end of the delivery wire;
  wherein the stent, when positioned in the compressed, elongated configuration on the distal portion of the delivery wire, has at least a portion extending proximal to the radio-opaque marker and is able to move freely past the radio-opaque marker along the delivery wire to be deployed in the lumen;
  and wherein the predetermined distance matches the unconstrained stent length of the expandable stent so as to indicate a proximal end location of the stent when the stent is in the shortened, unconstrained state;
  locating the terminal distal end of the micro-catheter at a delivery location distal to the treatment location such that the radio-opaque marker is aligned at a location proximal to the treatment location;
  extracting the stent from the terminal distal end of the micro-catheter such that the distal end of the stent is positioned in the expanded state at the delivery location;
  and retracting the micro-catheter proximally within the lumen as the stent is extracted from the terminal distal end of the micro-catheter such that the expanded stent spans the treatment location with a proximal end of the stent being substantially aligned with the proximal location of the radio-opaque marker upon being fully extracted from the micro-catheter.

18. A method as recited in claim 17, wherein the stent is delivered to the treatment location, wherein the treatment location comprises an aneurysm within a cerebral blood vessel; and wherein the delivery location is selected such that the stent spans across the aneurysm when disposed at the treatment location in the unconstrained state.

19. A method for precision delivery of a stent within a lumen of the body, comprising:
  positioning a terminal distal end of a micro-catheter to a treatment location within the lumen;
  delivering an expandable stent in a compressed, elongated configuration through the micro-catheter to the terminal distal end of the micro-catheter;
  wherein the micro-catheter comprises three or more radio-opaque markers disposed at spaced-apart intervals from the terminal distal end of the micro-catheter;
  wherein the radio-opaque markers are positioned such that the stent, when disposed within the micro-catheter in the compressed, elongated configuration, has at least a portion extending proximal to the radio-opaque markers and is able to move freely past the radio-opaque markers along the micro-catheter;
  and wherein the three or more radio-opaque markers comprise a first marker positioned a distance from the terminal distal end of the micro-catheter that matches the unconstrained stent length, a remainder of the three or more radio-opaque markers being positioned at said spaced-apart marker intervals, wherein the first marker indicates to a proximal end location of the stent when the stent is delivered to the treatment location in the shortened, unconstrained state after exiting the terminal distal end of the micro-catheter;
  locating the terminal distal end of the micro-catheter at a delivery location distal to the treatment location such that the first marker is aligned at a location proximal to the treatment location;
  extracting the stent from the terminal distal end of the micro-catheter such that a distal end of the stent is positioned in the expanded state at the delivery location;
  and retracting the micro-catheter proximally within the lumen as the stent is extracted from the terminal distal end of the micro-catheter such that the expanded stent spans the treatment location with a proximal end of the stent being substantially aligned with the location of the first marker upon being fully extracted from the micro-catheter.

20. A method as recited in claim 19, wherein the spaced-apart marker intervals form a ruler visible under radiographic imaging.

21. A method as recited in claim 19, wherein the micro-catheter is sized to allow delivery of the stent through the micro-catheter in the compressed, elongated configuration to the treatment location within the lumen.

22. A method as recited in claim 21, wherein the treatment location comprises an aneurysm within a cerebral blood vessel; and wherein the delivery location is selected such that the stent spans across the aneurysm when disposed at the treatment location in the unconstrained state.

* * * * *